United States Patent
Kawasaki et al.

(10) Patent No.: US 11,534,105 B2
(45) Date of Patent: Dec. 27, 2022

(54) ESTIMATION METHOD, ESTIMATION MODEL GENERATION METHOD, PROGRAM, AND ESTIMATION DEVICE

(71) Applicants: KEIO UNIVERSITY, Tokyo (JP); KOSE Corporation, Tokyo (JP)

(72) Inventors: Hiroshi Kawasaki, Tokyo (JP); Eiryo Kawakami, Tokyo (JP); Keita Koseki, Tokyo (JP); Tamotsu Ebihara, Tokyo (JP); Masayuki Amagai, Tokyo (JP); Eiji Naru, Tokyo (JP); Makoto Mizuno, Tokyo (JP); Miki Ito, Tokyo (JP); Toru Atsugi, Tokyo (JP); Yukako Kimura, Tokyo (JP)

(73) Assignees: KEIO UNIVERSITY, Tokyo (JP); KOSE Corporation, Tokyo (JP)

( * ) Notice: Subject to any disclaimer, the term of this patent is extended or adjusted under 35 U.S.C. 154(b) by 0 days.

(21) Appl. No.: 17/593,346

(22) PCT Filed: Mar. 19, 2020

(86) PCT No.: PCT/JP2020/012249
§ 371 (c)(1),
(2) Date: Sep. 16, 2021

(87) PCT Pub. No.: WO2020/189754
PCT Pub. Date: Sep. 24, 2020

(65) Prior Publication Data
US 2022/0142561 A1    May 12, 2022

(30) Foreign Application Priority Data

Mar. 20, 2019    (JP) ............................. JP2019-053776

(51) Int. Cl.
*A61B 5/00*    (2006.01)
*G06T 7/90*    (2017.01)
(Continued)

(52) U.S. Cl.
CPC ............ *A61B 5/441* (2013.01); *G06T 7/0012* (2013.01); *G06T 7/90* (2017.01); *G16H 30/20* (2018.01)

(58) Field of Classification Search
None
See application file for complete search history.

(56) References Cited

U.S. PATENT DOCUMENTS

| | | | |
|---|---|---|---|
| 10,667,744 B2* | 6/2020 | Arai | A61B 5/442 |
| 2018/0035941 A1* | 2/2018 | Shin | A61B 5/103 |

(Continued)

FOREIGN PATENT DOCUMENTS

| | | |
|---|---|---|
| CN | 102846309 A | 1/2013 |
| CN | 104887183 A | 9/2015 |

(Continued)

OTHER PUBLICATIONS

Liu, Y., Wang, Y., & Zhang, J. (Sep. 2012). New machine learning algorithm: Random forest. In International Conference on Information Computing and Applications (pp. 246-252). Springer, Berlin, Heidelberg. (Year: 2012).*

(Continued)

*Primary Examiner* — Samah A Beg
(74) *Attorney, Agent, or Firm* — Kenja IP Law PC

(57) ABSTRACT

An estimation method for estimating a parameter related to skin function is provided. The estimation method includes an image acquisition step for acquiring a skin image in which unevenness of a skin surface is captured; an extraction step for extracting a feature vector based on topological information on the skin image from the skin image acquired in the image acquisition step; an estimation step for estimating the parameter related to skin function based on the feature vector extracted in the extraction step, using an estimation model constructed based on past actual measure- (Continued)

ment data in which feature vectors are associated with the parameter related to skin function; and a presentation step for presenting the parameter related to skin function estimated in the estimation step.

10 Claims, 12 Drawing Sheets

(51) Int. Cl.
*G06T 7/00* (2017.01)
*G16H 30/20* (2018.01)

(56) References Cited

U.S. PATENT DOCUMENTS

| | | | | |
|---|---|---|---|---|
| 2018/0103915 | A1* | 4/2018 | Uehara | A61B 5/441 |
| 2019/0125247 | A1* | 5/2019 | Saeki | A61B 5/0285 |
| 2019/0149803 | A1* | 5/2019 | Ming | A61B 5/0064 348/47 |
| 2021/0137445 | A1* | 5/2021 | Park | A61B 5/0075 |
| 2022/0023355 | A1* | 1/2022 | Ito | A61P 17/04 |

FOREIGN PATENT DOCUMENTS

| | | | |
|---|---|---|---|
| JP | 2006223366 A | | 8/2006 |
| JP | 2012519894 A | | 8/2012 |
| JP | 2013090752 A | | 5/2013 |
| JP | 6035268 B2 | | 11/2016 |
| JP | 6058902 B2 | | 1/2017 |
| JP | 2017199384 A | | 11/2017 |
| JP | 2018531437 A | | 10/2018 |
| KR | 20180042657 A | * | 4/2018 |
| KR | 1020180107209 A | | 10/2018 |

OTHER PUBLICATIONS

Koseki, Keita, et al. "Assessment of skin barrier function using skin images with topological data analysis." NPJ systems biology and applications 6.1 (2020): 1-9. (Year: 2020).*
Sep. 16, 2021, International Preliminary Reporton Patentability issued in the International Patent Application No. PCT/JP2020/012249.
Dec. 27, 2021, Office Action issued by the China National Intellectual Property Administration in the corresponding Chinese Patent Application No. 202080020708.7.
Jan. 5, 2022, Office Action issued by the Taiwan Intellectual Property Office in the corresponding Taiwanese Patent Application No. 109109282.
Jan. 7, 2022, Office Action issued by the Korean Intellectual Property Office in the corresponding Korean Patent Application No. 10-2021-7028038.
Jun. 9, 2020, Written Opinion of the International Searching Authority issued in the International Patent Application No. PCT/JP2020/012249.
Jun. 9, 2020, International Search Report issued in the International Patent Application No. PCT/JP2020/012249.
Kenzo Kitajima, 2014 Master'S Thesis, Establishment of Quantitative Index of Skin Condition Using Image Analysis, Mar. 24, 2015, Department of Applied Informatics, Hosei University Graduate School Faculty of Science and Engineering, with a partial English translation.

* cited by examiner

ESTIMATION METHOD, ESTIMATION MODEL GENERATION METHOD, PROGRAM, AND ESTIMATION DEVICE

CROSS-REFERENCE TO RELATED APPLICATION

This application claims priority to Japanese Patent Application No. 2019-053776, filed on Mar. 20, 2019, the entire contents of which are incorporated herein by reference.

TECHNICAL FIELD

The disclosure relates to an estimation method, an estimation model generation method, a program, and an estimation device.

BACKGROUND

Technology for analyzing the condition of biological tissues is known.

For example, Patent Literature (PTL) 1 discloses an operation method for an optical transmission diagnostic device in which a plurality of LEDs (Light Emitting Diodes), each emitting a light ray of a different wavelength, are arranged at different angles to skin, in order to assist in distinguishing between benign tissues and malignant tissues based on a measured reflectance spectrum. The operation method for the optical transmission diagnostic device relates to an optical method for determining some of morphological parameters and physiological properties of biological tissues, and in particular to a method for determining the morphological parameters and physiological properties of benign and malignant tissue lesions.

For example, Patent Literature (PTL) 2 discloses a skin condition analysis method that analyzes the condition of a skin surface based on the shape of skin grooves on the skin surface. In the skin condition analysis method, a plurality of optical cross-sectional images, which are three-dimensional shape data of the skin grooves on the skin surface, are acquired using a confocal microscope, and the condition of the skin surface is evaluated.

For example, in recent years, skin barrier dysfunction caused by filaggrin gene abnormality or the like receives attention as a mechanism for the development of atopic dermatitis. Transepidermal water loss (TEWL) is mainly used as an example of an index of skin barrier function. For example, if the skin barrier function is high, TEWL is low. Conversely, if the skin barrier function is low, TEWL is high.

CITATION LIST

Patent Literatures

PTL 1: JP 6035268 B2
PTL 2: JP 6058902 B2

SUMMARY

Technical Problem

In the conventional technology described in PTL 1 and PTL 2, analysis of the condition of biological tissues is considered, but the function of biological tissues including skin barrier function and the like, not the condition of biological tissues, is not considered. Therefore, the conventional technology does not take into account the estimation of the function of biological tissues. On the other hand, there is a demand for accurate estimation of parameters related to skin function including TEWL and the like, for the purpose of accurate estimation of the function of biological tissues including skin barrier function and the like.

It would be helpful to provide an estimation method, an estimation model generation method, a program, and an estimation device that enable accurate estimation of a parameter related to skin function.

Solution to Problem

To solve the above-described problems, an estimation method according to an embodiment of the disclosure is an estimation method for estimating a parameter related to skin function, the estimation method including:

an image acquisition step for acquiring a skin image in which unevenness of a skin surface is captured;

an extraction step for extracting a feature vector based on topological information on the skin image from the skin image acquired in the image acquisition step;

an estimation step for estimating the parameter related to skin function based on the feature vector extracted in the extraction step, using an estimation model constructed based on past actual measurement data in which a feature vector is associated with the parameter related to skin function; and a presentation step for presenting the parameter related to skin function estimated in the estimation step.

To solve the above-described problems, an estimation model generation method according to an embodiment of the disclosure is an estimation method generation method for generating the estimation model used in the above-described estimation method, the estimation model generation method including:

an acquisition step for acquiring the past actual measurement data in which the feature vector is associated with the parameter related to skin function; and a construction step for constructing, based on the past actual measurement data acquired in the acquisition step, the estimation model to estimate the parameter related to skin function based on the feature vector.

To solve the above-described problems, a program according to an embodiment of the disclosure is configured to cause an information processing device to execute the above-described estimation method or the above-described estimation model generation method.

To solve the above-described problems, an estimation device according to an embodiment of the disclosure is an estimation device for estimating a parameter related to skin function, the estimation device including:

an image acquisition unit configured to acquire a skin image in which unevenness of a skin surface is captured;

a controller configured to extract a feature vector based on topological information on the skin image from the skin image acquired by the image acquisition unit, and estimate the parameter related to skin function based on the extracted feature vector using an estimation model constructed based on past actual measurement data in which a feature vector is associated with the parameter related to skin function; and a presentation unit configured to present the parameter related to skin function estimated by the controller.

Advantageous Effect

According to an estimation method, an estimation model generation method, a program, and an estimation device according to an embodiment of the disclosure, it is possible to accurately estimate a parameter related to skin function.

BRIEF DESCRIPTION OF THE DRAWINGS

In the accompanying drawings:

FIG. 1 is a flowchart illustrating an example of a first operation by the estimation device of FIG. 1;

FIG. 7 is a schematic diagram illustrating an estimation model based on random forest according to the embodiment;

DETAILED DESCRIPTION

An embodiment of the disclosure will be described in detail below with reference to the accompanying drawings.

Figure 1:
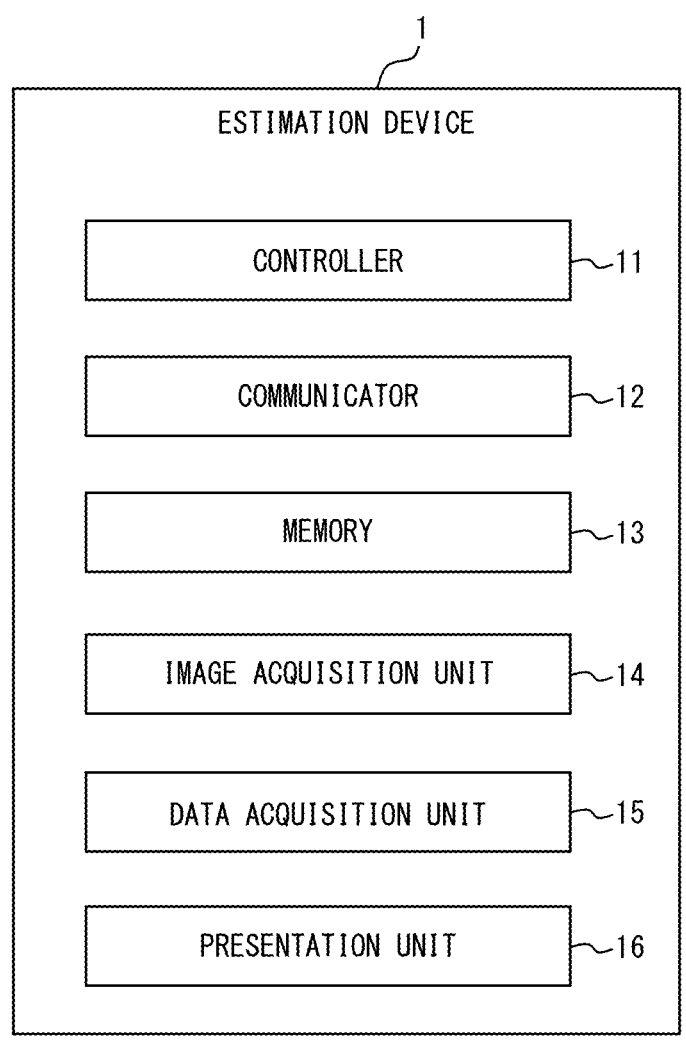
FIG. 1 is a block diagram illustrating a schematic configuration of an estimation device according to an embodiment of the disclosure.

FIG. 1 is a block diagram illustrating a schematic configuration of an estimation device 1 according to the embodiment of the disclosure. With reference to FIG. 1, the configuration and functions of the estimation device 1 according to the embodiment of the disclosure will be mainly described.

As an outline of the embodiment, the estimation device 1 acquires a skin image in which unevenness of a skin surface is captured. The estimation device 1 extracts, from the acquired skin image, a feature vector based on topological information on the skin image. The estimation device 1 estimates a parameter related to skin function based on the extracted feature vector, using an estimation model constructed based on past actual measurement data in which feature vectors are associated with the parameter related to skin function. The estimation device 1 presents the estimated parameter related to skin function. The parameter related to skin function includes, for example, TEWL. Not limited to this, the parameter related to skin function may include any index associated with the function of biological tissues, including skin barrier function or the like. For example, the parameter related to skin function may include moisture content of skin.

The estimation device 1 is, for example, an electronic device that estimates a parameter related to skin function based on a skin image in which unevenness of a human's skin surface is captured. For example, the estimation device 1 may be a dedicated electronic device or any general-purpose electronic device, such as a smartphone, a PC (Personal Computer), or a server device. For example, the estimation device 1 may acquire a skin image by imaging a human's skin surface by itself and estimate a parameter related to skin function based on the skin image. Not limited to this, for example, the estimation device 1 may acquire a skin image of a human's skin surface captured by another imaging device or the like from the imaging device or the like by any means such as communication, and estimate a parameter related to skin function based on the acquired skin image.

As illustrated in FIG. 1, the estimation device 1 has a controller 11, a communicator 12, a memory 13, an image acquisition unit 14, a data acquisition unit 15, and a presentation unit 16.

The controller 11 includes one or more processors. In the embodiment, a "processor" is a general-purpose processor or a dedicated processor specialized for a particular processing, but is not limited to these. The controller 11 is communicably connected to each of the components of the estimation device 1, and controls the operation of the entire estimation device 1.

In the embodiment, for example, the controller 11 may control the communicator 12 to transmit an estimation result by the estimation device 1 to any other information processing device. For example, the controller 11 may control the memory 13 to store an estimation result by the estimation device 1 and an acquired skin image. For example, the controller 11 may control the image acquisition unit 14 to acquire a skin image in which unevenness of a skin surface is captured. For example, the controller 11 may control the data acquisition unit 15 to acquire past actual measurement data in which feature vectors are associated with a parameter related to skin function. For example, the controller 11 may control the presentation unit 16 to present an estimation result by the estimation device 1 to a user.

The communicator 12 includes a communication module connecting to a network, including a mobile communication network, the Internet, or the like. For example, the communicator 12 may include a communication module conforming to mobile communication standards such as 4G (4th Generation) standards or 5G (5th Generation) standards. For example, the communicator 12 may include a communication module conforming to wired LAN (Local Area Network) standards.

The memory 13 includes one or more memory devices. In the embodiment, a "memory device" is, for example, a semiconductor memory device, a magnetic memory device, an optical memory device, or the like, but is not limited to these. Each memory device included in the memory 13 may function as, for example, a main memory, an auxiliary memory, or a cache memory. The memory 13 stores any information used in operation of the estimation device 1. For example, the memory 13 may store a system program, an application program, various types of information acquired by the estimation device 1, an estimation result by the estimation device 1, and the like. The information stored in the memory 13 may be updatable with information acquired from a network via the communicator 12, for example.

The image acquisition unit 14 includes any imaging device such as a camera, for example. The image acquisition unit 14 may acquire a skin image in which unevenness of a skin surface is captured, for example, by imaging using the imaging device in possession of the image acquisition unit 14 itself. Not limited to this, the image acquisition unit 14 may acquire a skin image in which unevenness of a skin surface is captured in any way. For example, the image acquisition unit 14 may acquire a skin image of a skin surface captured by another imaging device or the like from the imaging device or the like by any means such as communication.

The data acquisition unit 15 includes, for example, any interface capable of acquiring past actual measurement data in which feature vectors are associated with a parameter related to skin function. For example, the data acquisition unit 15 may include an any input interface capable of accepting an input operation by a user, and acquire actual measurement data based on input by the user. For example, the data acquisition unit 15 may include any communication interface, and acquire actual measurement data from an external device or the like by any communication protocol.

The presentation unit 16 includes any output interface that outputs an image, for example. The presentation unit 16 includes, for example, any display such as a liquid crystal display or an organic EL (Electro Luminescence) display. The presentation unit 16 presents an estimation result by the estimation device 1 to a user or the like. For example, the presentation unit 16 presents a parameter related to skin function estimated by the controller 11 of the estimation device 1.

Figure 2:
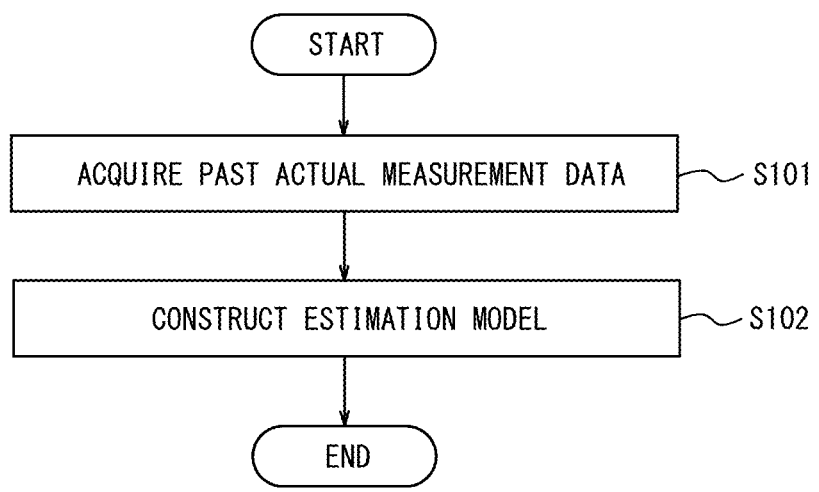
FIG. 2 is a flowchart illustrating an example of a second operation by the estimation device of FIG. 1.

FIG. 2 is a flowchart illustrating an example of a first operation by the estimation device 1 of FIG. 1. FIG. 2 illustrates a flow in which the estimation device 1 generates an estimation model based on past actual measurement data. In other words, FIG. 2 illustrates an estimation model generation method used in an estimation method, which will be described later, using the estimation device 1.

In step S101, the controller 11 of the estimation device 1 acquires, using the data acquisition unit 15, past actual measurement data in which feature vectors are associated with a parameter related to skin function.

In step S102, the controller 11 constructs an estimation model to estimate the parameter related to skin function based on a feature vector, based on the past actual measurement data acquired in step S101.

The estimation model may be, for example, a machine learning model including a random forest model learned based on the past actual measurement data acquired in step S101. Not limited to this, the estimation model may be any machine learning model including a neural network, a local regression model, a kernel regression model, and the like.

Figure 3:
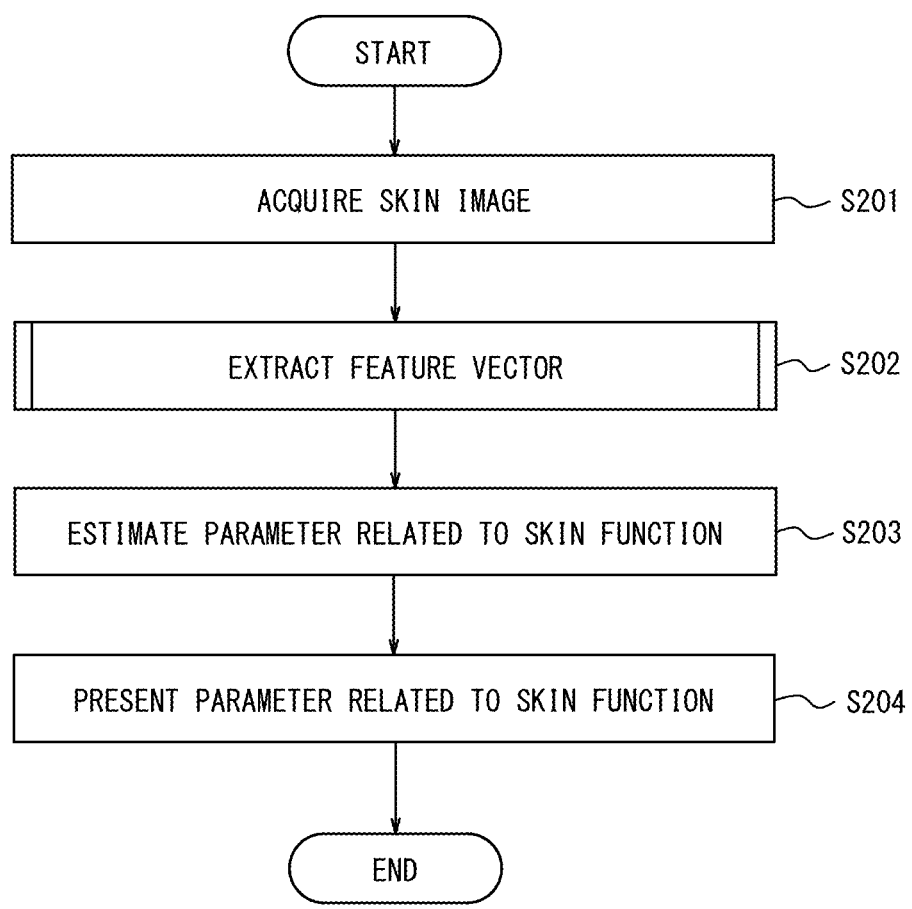
FIG. 3 is a flowchart illustrating an example of a third operation by the estimation device of FIG. 1.

FIG. 3 is a flowchart illustrating an example of a second operation by the estimation device 1 of FIG. 1. FIG. 3 mainly illustrates a flow in which the estimation device 1 estimates a parameter related to skin function using an estimation model constructed by the flow in FIG. 2. In other words, FIG. 3 illustrates an estimation method for estimating a parameter related to skin function using the estimation device 1.

In step S201, the controller 11 of the estimation device 1 acquires, using the image acquisition unit 14, a skin image in which unevenness of a skin surface is captured.

In step S202, the controller 11 extracts a feature vector based on topological information on the skin image from the skin image acquired in step S201. Since step S202 includes a more detailed flow as described later in FIG. 4, the box of step S202 is indicated with double lines in FIG. 3.

In step S203, the controller 11 estimates a parameter related to skin function based on the feature vector extracted in step S202, using an estimation model constructed by the flow of FIG. 2.

In step S204, the controller 11 presents, using the presentation unit 16, the parameter related to skin function estimated in step S203.

Figure 4:
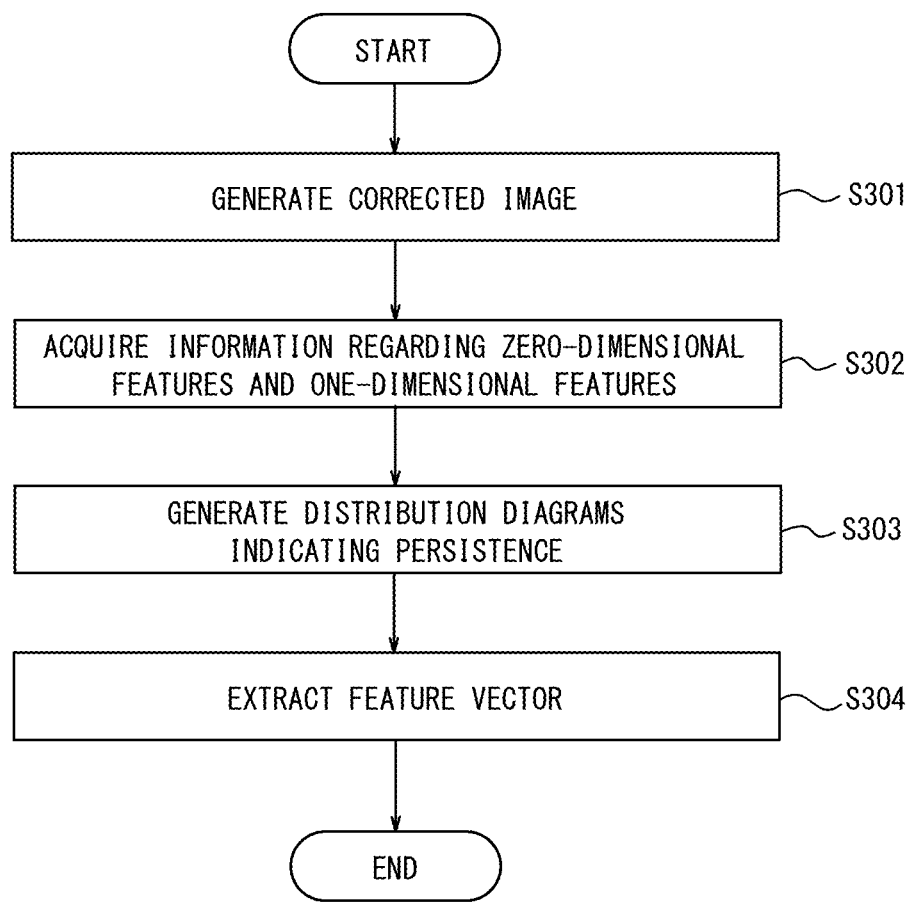
FIG. 4 is a schematic diagram illustrating an example of a corrected image generated in step S301 of FIG. 4.

FIG. 4 is a flowchart illustrating an example of a third operation by the estimation device 1 of FIG. 1. FIG. 4 illustrates the flow in step S202 of FIG. 3 in more detail. With reference to FIG. 4, the flow until the controller 11 of the estimation device 1 extracts a feature vector based on an acquired skin image will be described in more detail.

Figure 5:
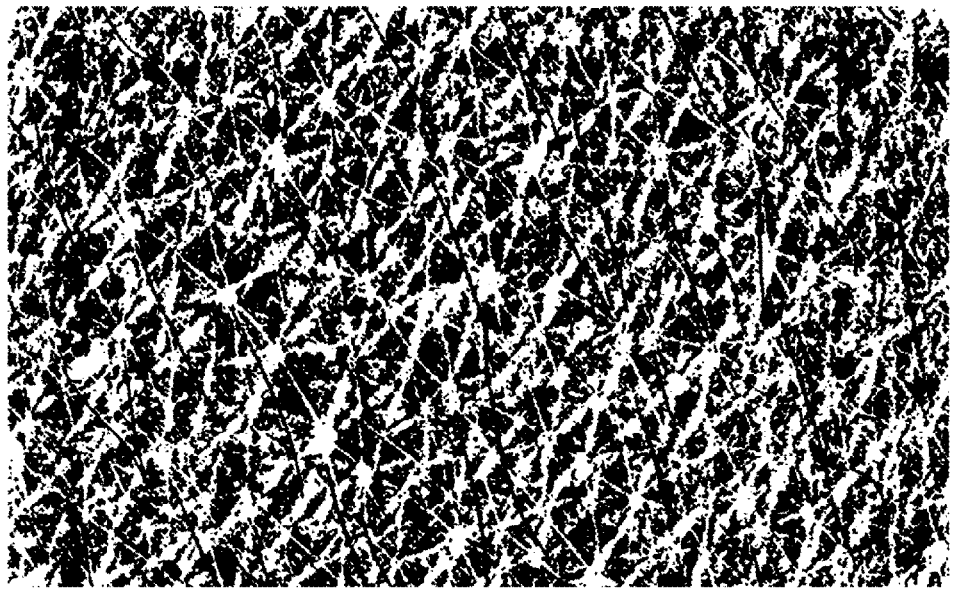
FIG. 5 is a schematic diagram illustrating an example of a method for acquiring topological information in step S302 of FIG. 4.

In step S301, the controller 11 of the estimation device 1 generates a corrected image by applying brightness correction processing and binarization processing to a skin image acquired in step S201 of FIG. 3. FIG. 5 is a schematic diagram illustrating an example of the corrected image generated in step S301 of FIG. 4.

The controller 11 uses, for example, a wavelet transform to generate the corrected image as illustrated in FIG. 5, which contains only information in a predetermined frequency domain. By generating such a corrected image, the controller 11 removes redundant information, which is not related to unevenness of a skin surface and can be noise, from the skin image acquired in step S201 of FIG. 3.

Figure 6:
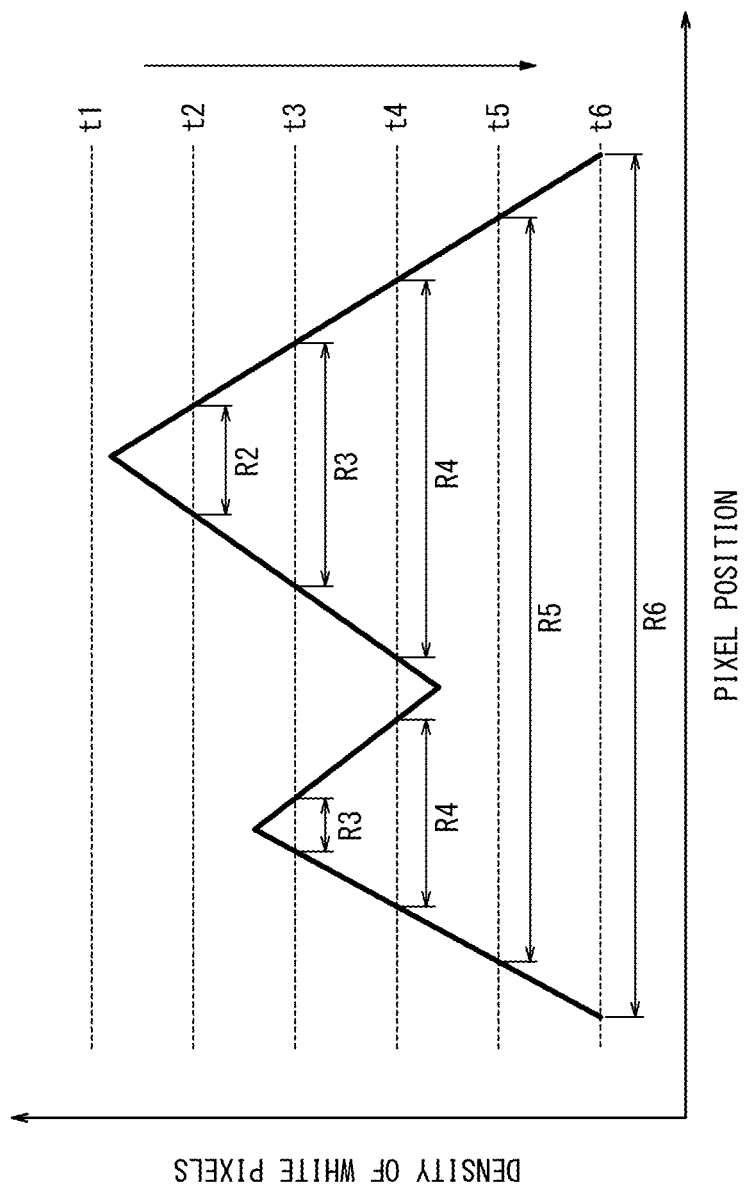
FIG. 6 is a distribution diagram illustrating an example of persistence of one-dimensional features.

In step S302 of FIG. 4, the controller 11 acquires information regarding zero-dimensional features and one-dimensional features extracted based on the corrected image generated in step S301. The information regarding the zero-dimensional features and the one-dimensional features constitutes the topological information described above. FIG. 6 is a schematic diagram illustrating an example of a method for acquiring the topological information in step S302 of FIG. 4. With reference to FIG. 6, a method by which the controller 11 extracts zero-dimensional features and one-dimensional features based on the corrected image generated in step S301 will be mainly described.

The controller 11 estimates the density of white pixels on the corrected image generated in step S301, and generates an image that represents the density of the white pixels relative to a pixel region as a topographic map. For example, in such an image, a variation in the density of white pixels is represented as a mountain in a pixel region in which the density of the white pixels is large, and as a valley in a pixel region in which the density of black pixels is large.

FIG. 6 is a schematic diagram in which a variation in the density of white pixels along a predetermined row of pixels is one-dimensionally illustrated in such an image. In FIG. 6, the vertical axis indicates the density of white pixels. The horizontal axis indicates pixel position.

The controller 11, for example, changes a threshold t of the density of white pixels in a graph illustrating a variation in the density of white pixels as illustrated in FIG. 6. For example, in a case in which the graph intersects a straight line corresponding to the threshold t as illustrated by the dashed line in FIG. 6, the controller 11 determines all pixels to be white for a pixel region in which the value of the density of white pixels in the graph is larger than the threshold t. For example, the controller 11 determines all pixels to be black for the other pixel regions.

Figure 7:
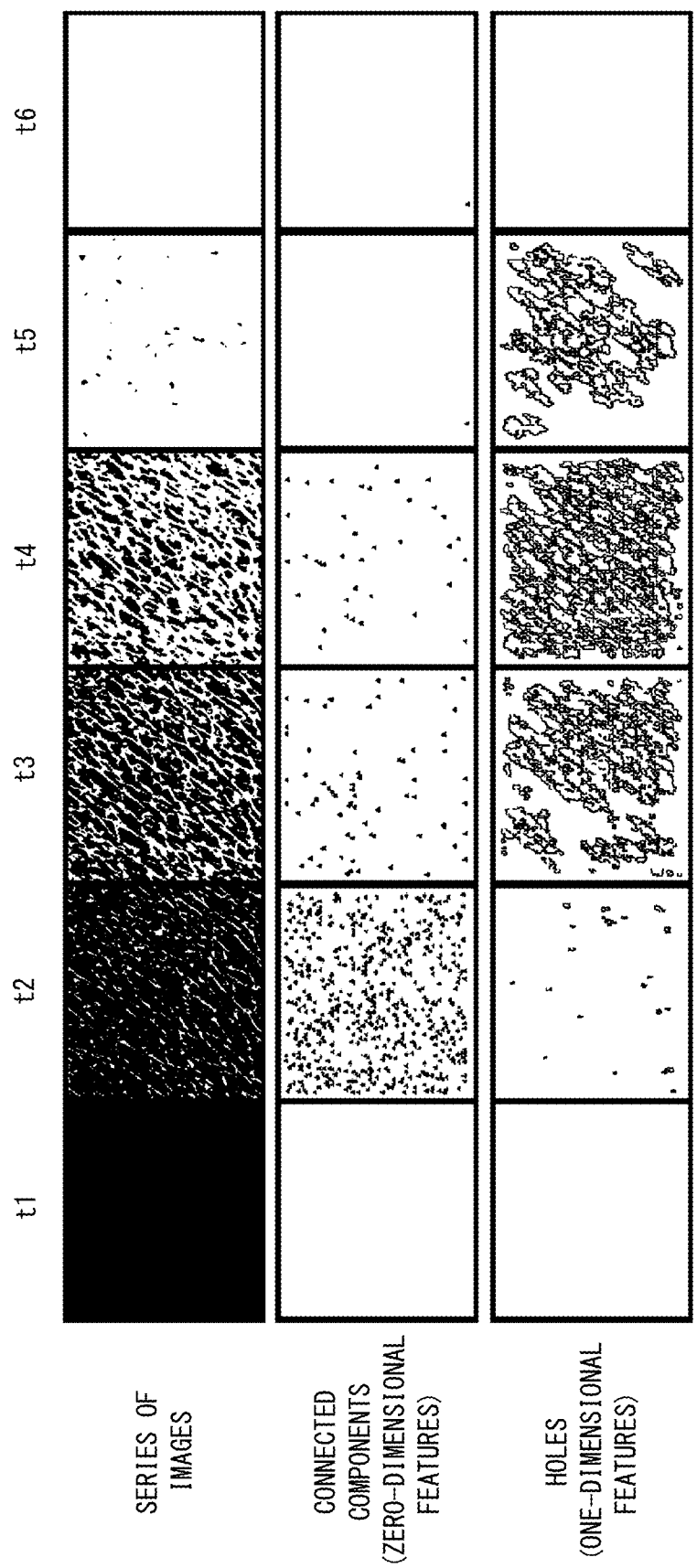
FIG. 7 is a schematic diagram illustrating an example of change in an image and the topological information, in the case of changing a threshold in steps.

FIG. 7 is a schematic diagram illustrating an example of change in an image and topological information in a case in which the threshold t is changed in steps. More specifically, a series of images in the top row of FIG. 7 illustrate change in the way of connection of white regions, in the case of changing the threshold t in steps. The middle row of FIG. 7 illustrates change in zero-dimensional features, in the case of changing the threshold t in steps. The bottom row of FIG. 7 illustrates change in one-dimensional features, in the case of changing the threshold tin steps.

For example, in a case in which the threshold t is determined at t1 in FIG. 6, the controller 11 determines all pixels in the image to be black because the straight line corresponding to the threshold t1 does not intersect with the graph. Therefore, as illustrated in the top row of FIG. 7, the image with the threshold t1 is such that the entire image is filled with black.

For example, in a case in which the controller 11 determines the threshold t at t2 in FIG. 6, the straight line corresponding to the threshold t2 intersects with the graph in a region R2, and the density of white pixels in the graph is larger in value than the threshold t2 in the region R2. Therefore, the controller 11 determines all pixels in the region R2 to be white. The controller 11 determines all pixels to be black in the pixel regions other than the region R2. Therefore, as illustrated in the top row of FIG. 7, the image with the threshold t2 is such that white regions slightly appear, but overall there are many black pixels.

For example, in a case in which the controller 11 determines the threshold t at t3 in FIG. 6, the straight line corresponding to the threshold t3 intersects with the graph in regions R3, and the density of white pixels in the graph is larger in value than the threshold t3 in the regions R3. Therefore, the controller 11 determines all pixels in the regions R3 to be white. The controller 11 determines all pixels to be black in the pixel regions other than the regions R3. Therefore, as illustrated in the top row of FIG. 7, the image with threshold t3 has more white regions than the image with the threshold t2.

For example, in a case in which the controller 11 determines the threshold t at t4 in FIG. 6, the straight line corresponding to the threshold t4 intersects with the graph in regions R4, and the density of white pixels in the graph is larger in value than the threshold t4 in the regions R4. Therefore, the controller 11 determines all pixels in the regions R4 to be white. The controller 11 determines all pixels to be black in the regions other than the regions R4. Therefore, as illustrated in the top row of FIG. 7, the image with the threshold t4 has even more white regions than the image with the threshold t3.

For example, in a case in which the controller 11 determines the threshold t at t5 in FIG. 6, the straight line corresponding to the threshold t5 intersects with the graph in a region R5, and the density of white pixels in the graph is larger in value than the threshold t5 in the region R5. Therefore, the controller 11 determines all pixels in the region R5 to be white. The controller 11 determines all pixels to be black in the regions other than the region R5. Therefore, as illustrated in the top row of FIG. 7, the image with the threshold t5 is such that overall there are many white pixels, though black regions slightly remain.

For example, in a case in which the controller 11 determines the threshold t at t6 in FIG. 6, the straight line corresponding to the threshold t6 entirely intersects with the graph in a region R6, and the density of white pixels in the graph is larger in value than the threshold t6 in the region R6. Therefore, the controller 11 determines all pixels in the region R6 to be white. Therefore, as illustrated in the top row of FIG. 7, the image with the threshold t6 is such that the entire image is filled with white.

As described above, the controller 11 gradually changes the threshold t and acquires a series of images that indicate change in the way of connection of white regions. The controller 11 extracts topological information including zero-dimensional features and one-dimensional features from the acquired series of images.

For example, as illustrated in the middle row of FIG. 7, the controller 11 extracts, as zero-dimensional features, portions in which white pixels are connected from the acquired series of images. Thus, the zero-dimensional features correspond to connected components in the series of images. For example, in the image with the threshold t1, the number of the zero-dimensional features is 0. For example, in the image with the threshold t6, the number of the zero-dimensional features is 1.

For example, as illustrated in the bottom row of FIG. 7, the controller 11 extracts, as one-dimensional features, portions in which a black pixel is present in the middle of white pixels by following the white pixels in the acquired series of images. In this way, the one-dimensional features correspond to holes in the series of images. For example, in each of the images with thresholds t1 and t6, the number of the one-dimensional features is 0.

The connected components and the holes extracted from the series of images illustrated in the top row of FIG. 7 appear and disappear as the threshold t changes. That is, if a connected component appears at a certain threshold $tb_c$, the connected component disappears at another threshold $td_c$ having a value smaller than the threshold $tb_c$. Similarly, if a hole appears at a certain threshold $tb_h$, the hole disappears at another threshold $td_h$ having a value smaller than the threshold $tb_h$.

The controller 11 stores a pair of thresholds $tb_c$ and $td_c$ for each connected component in the memory 13. Similarly, the controller 11 stores a pair of thresholds $tb_h$ and $td_h$ for each hole in the memory 13.

In step S303 of FIG. 4, the controller 11 generates a distribution diagram indicating the persistence of each of the zero-dimensional features based on the pair of thresholds $tb_c$ and $td_c$ stored in the memory 13. Similarly, the controller 11 generates a distribution diagram indicating the persistence of each of the one-dimensional features based on the pair of thresholds $tb_h$ and $td_h$ stored in the memory 13. The controller 11 may generate a distribution diagram indicating the persistence of each of the zero-dimensional features and the one-dimensional features, for example, based on one skin image acquired in step S201 of FIG. 3. Not limited to this, the controller 11 may generate a distribution diagram indicating the persistence of each of the zero-dimensional features and the one-dimensional features, for example, based on a plurality of skin images acquired in step S201 of FIG. 3.

Figure 8:
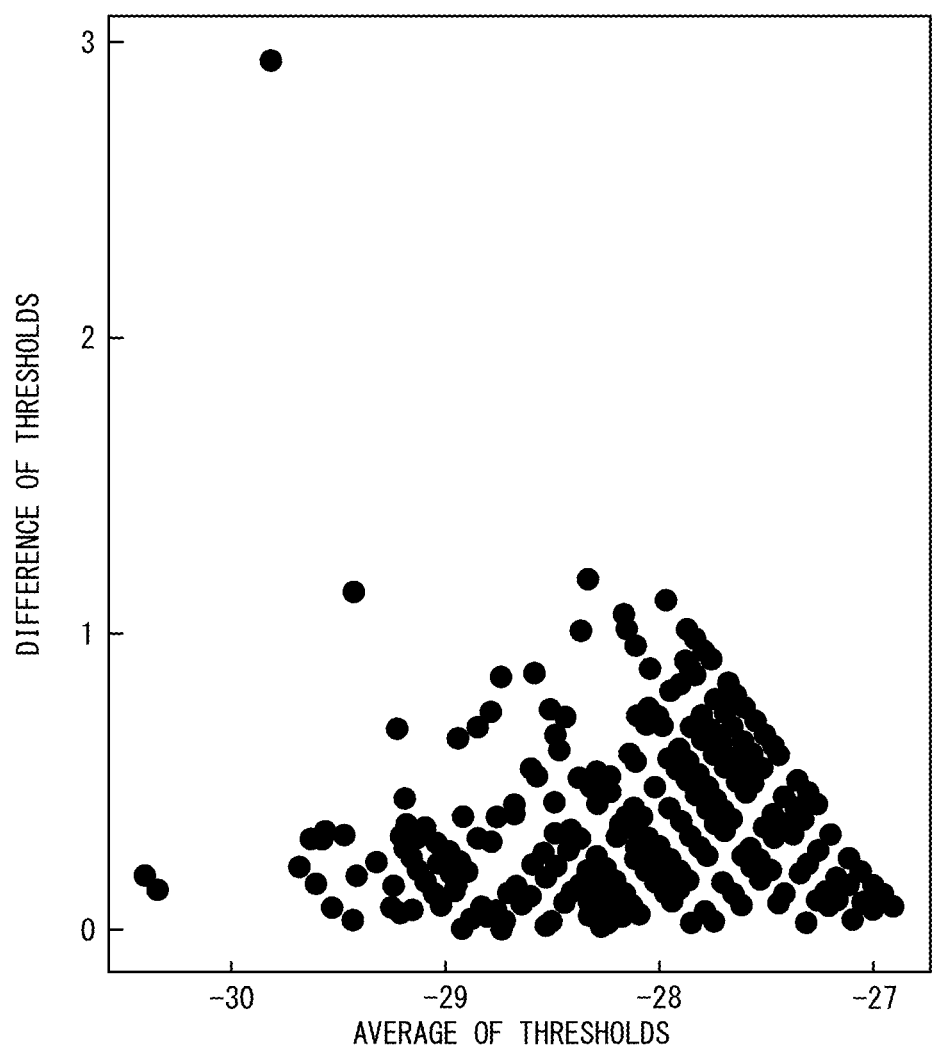
FIG. 8 is a distribution diagram illustrating an example of persistence of zero-dimensional features.

FIG. 8 is a distribution diagram illustrating an example of the persistence of the zero-dimensional features. In FIG. 8, the vertical axis represents the difference between the threshold $tb_c$ and the threshold $td_c$. In other words, the vertical axis of FIG. 8 provides a scale of persistence, i.e. the extent to which the zero-dimensional feature persists in response to change in the threshold t. In FIG. 8, the horizontal axis represents the average between the threshold $tb_c$ and the threshold $td_c$. In other words, the horizontal axis of FIG. 8 provides an indication at which threshold t the zero-dimensional feature is present in response to change in the threshold t. In the distribution diagram of FIG. 8, every dot is plotted in the same manner for the purpose of simple illustration, but the value of the density of the zero-dimensional feature is different at each dot. For example, each dot can have any density value. In other words, a predetermined number of zero-dimensional features are overlapped at each dot.

Figure 9:
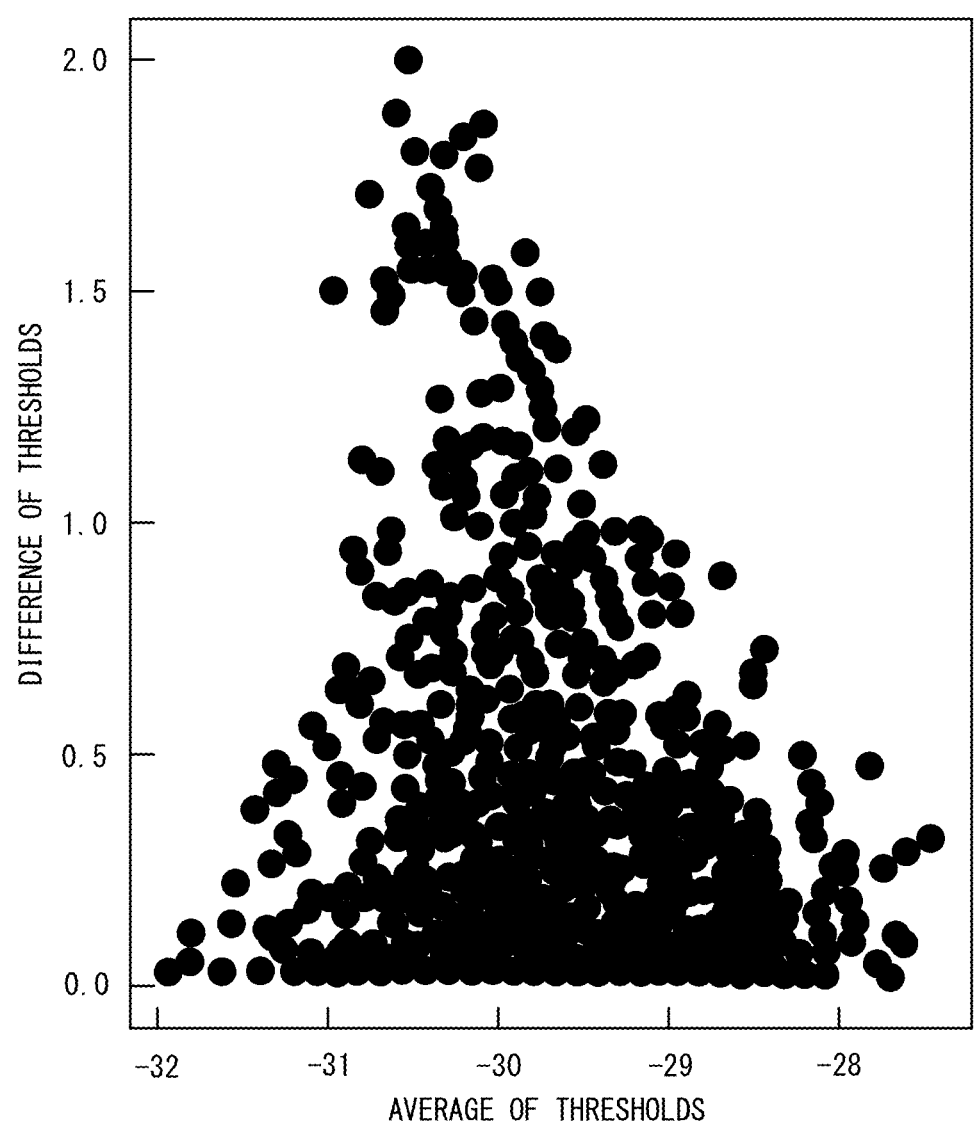

FIG. 9 is a distribution diagram illustrating an example of the persistence of the one-dimensional features. In FIG. 9, the vertical axis represents the difference between the threshold $tb_h$ and the threshold $td_h$. In other words, the vertical axis of FIG. 9 provides a scale of persistence, i.e. the extent to which the one-dimensional feature persists in response to change in the threshold t. In FIG. 9, the horizontal axis represents the average between the threshold $tb_h$ and the threshold $td_h$. In other words, the horizontal axis of FIG. 9 provides an indication at which threshold t the one-dimensional feature is present in response to change in the threshold t. In the distribution diagram of FIG. 9, every dot is plotted in the same manner for the purpose of simple illustration, but the value of the density of the one-dimensional feature is different at each dot. For example, each dot can have any density value. In other words, a predetermined number of one-dimensional features are overlapped at each dot.

In step S304 of FIG. 4, the controller 11 extracts a feature vector based on the distribution diagrams generated in step S303.

Figure 10:
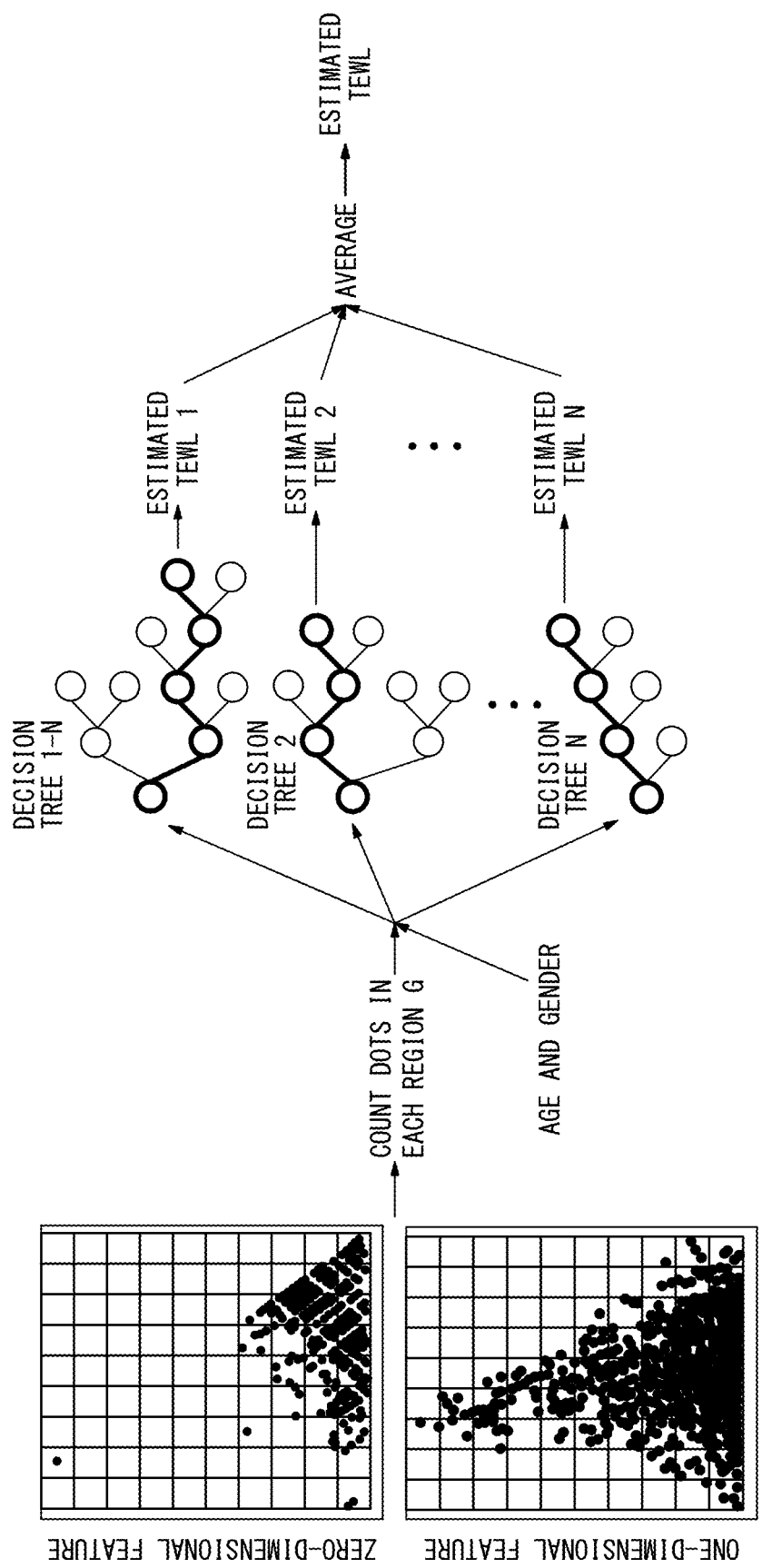

FIG. 10 is a schematic diagram of an estimation model based on random forest according to the embodiment. With reference to FIG. 10, an example of a method for extracting a feature vector in step S304 of FIG. 4 and a method for estimating a parameter related to skin function in step S203 of FIG. 3 will be mainly explained.

In step S304 of FIG. 4, the controller 11 defines a grid in each of the distribution diagrams of the zero-dimensional features and the one-dimensional features generated in step S303, and sets a plurality of regions G. The controller 11 calculates the number of dots included in each of the plurality of set regions G for each region G. The controller 11 extracts, as a feature vector, a vector in which the calculated numbers of dots are arranged for the respective regions G. At this time, the density value of each dot in the distribution diagrams of the zero-dimensional features and the one-dimensional features may be taken into account.

The controller 11 estimates a parameter related to skin function based on the feature vector extracted through the flow of FIG. 4 using an estimation model constructed by the flow of FIG. 2. More specifically, the controller 11 estimates a parameter related to skin function using a machine learning model including a random forest model. At this time, the controller 11 may estimate a parameter related to skin function based on, for example, an attribute of a subject, in addition to the feature vector extracted through the flow of FIG. 4. The attribute of the subject may include the age and gender of the subject, for example.

As illustrated in FIG. 10, for example, the controller 11 randomly selects one or more components of the feature vector extracted through the flow of FIG. 4. For example, the controller 11 associates the randomly selected one or more components of the feature vector with a decision tree 1. For example, the controller 11 performs the same process for a plurality of decision trees from a decision tree 2 to a decision tree N. The controller 11 estimates a value of TEWL, using the components of the feature vector associated with the respective decision trees as variables. The controller 11 averages a plurality of values of TEWL estimated for the plurality of respective decision trees, to estimate a final value of TEWL.

Figure 11:
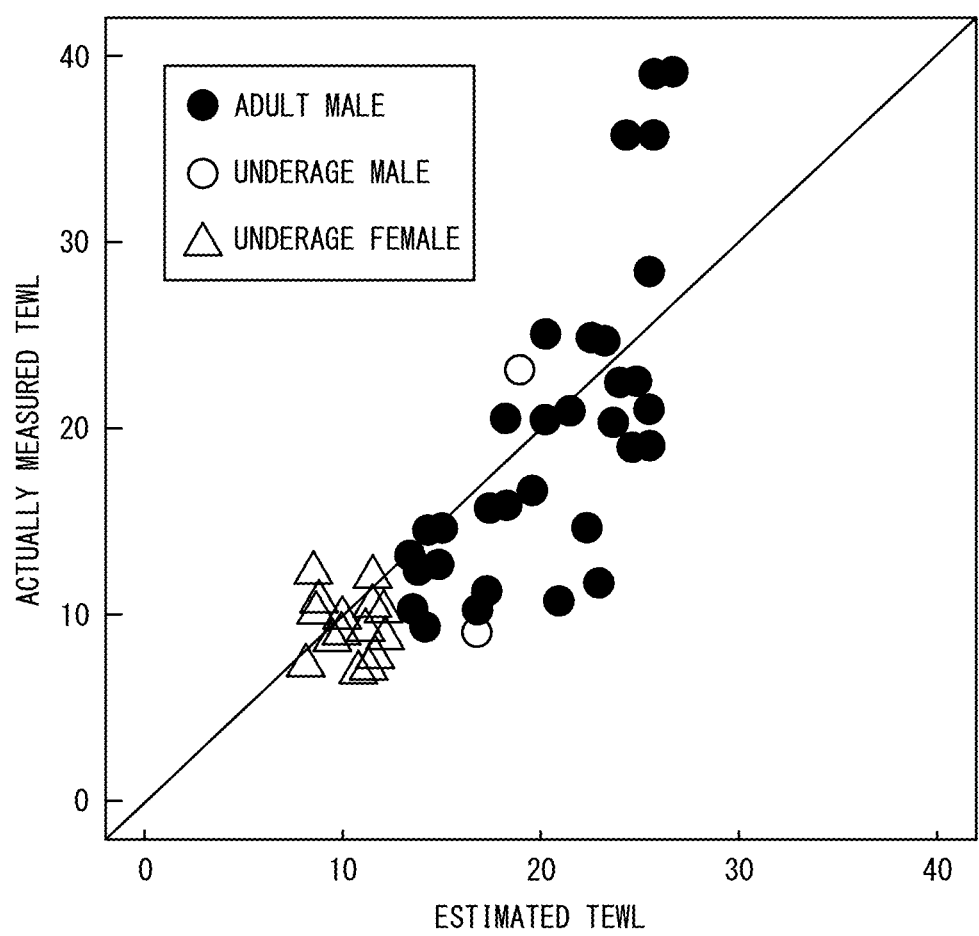
FIG. 11 is a scatter plot illustrating an example of first estimation results by the estimation device of FIG. 1.

FIG. 11 is a scatter plot indicating an example of first estimation results by the estimation device 1 of FIG. 1. In FIG. 11, the vertical axis represents an actually measured value of TEWL. The horizontal axis represents an estimated value of TEWL. Black circles represent data in the case of using skin images of adult males. The adult males include males aged 20 years or older. White circles represent data in the case of using skin images of underage males. The underage males include males between the ages of 0 and 19 inclusive. White triangles represent data in the case of using skin images of underage females. The underage females include females between the ages of 0 and 19 inclusive.

As illustrated in FIG. 11, in the estimation results by the estimation device 1, the actually measured values of TEWL and the estimated values thereof have good correspondences. In other words, the difference between a value of TEWL estimated using the estimation device 1 and an actually measured value of TEWL is within a predetermined error range. A coefficient of determination in this case was 0.667. In addition, a regression analysis with TEWL, which is considered to reflect skin barrier function, resulted in a strong correlation between the two. As another example of a parameter related to skin function, the same analysis was conducted for moisture content of skin, and a correlation was also found between the two.

Figure 12:
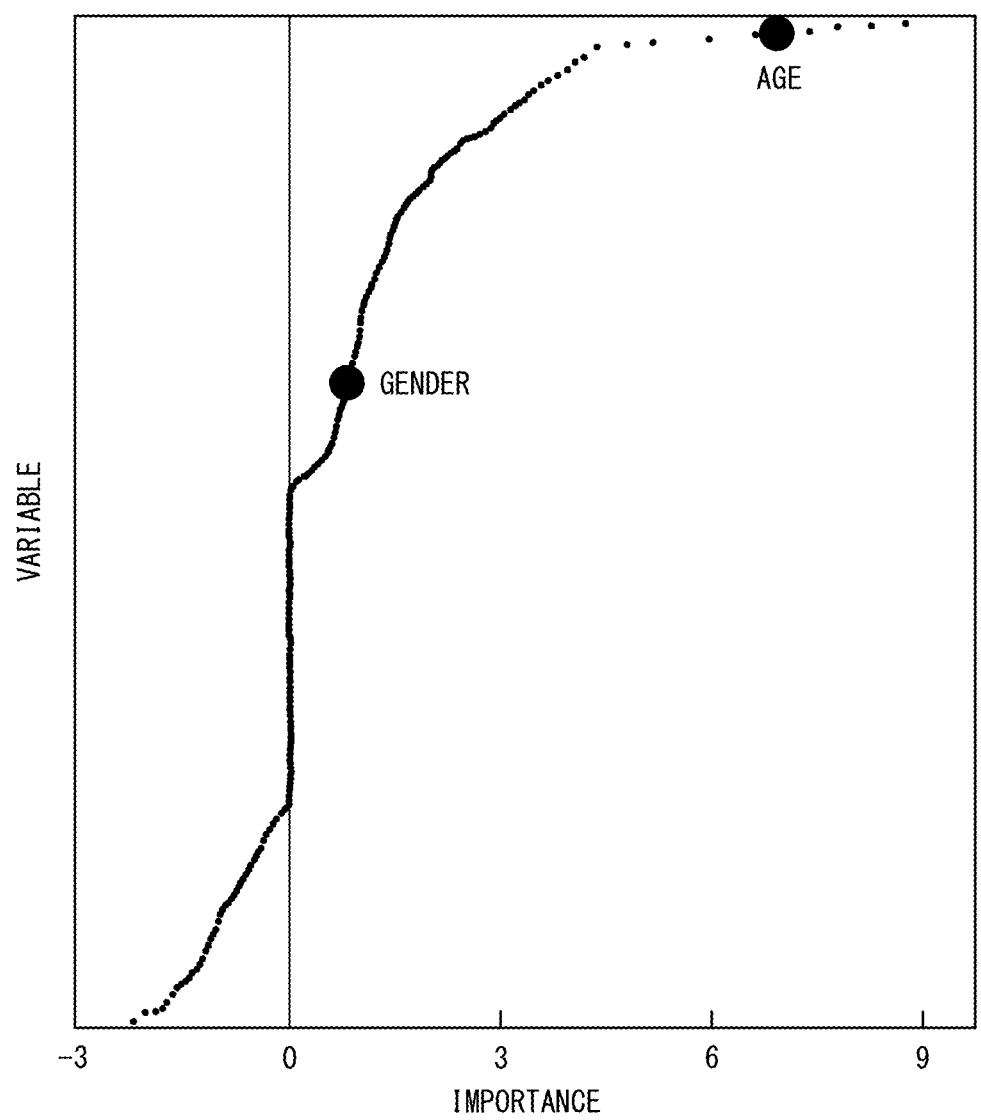
FIG. 12 is a graph illustrating an example of second estimation results by the estimation device of FIG. 1.

FIG. 12 is a graph illustrating an example of second estimation results by the estimation device 1 of FIG. 1. In FIG. 12, the vertical axis represents the types of variables. The horizontal axis represents the importance of the variables.

The estimation device 1 can also provide the importance of variables in estimation results. For example, in a case in which the controller 11 estimates a parameter related to skin function based on attributes of a subject, in addition to a feature vector, the estimation device 1 can also use age and gender as variables in addition to components of the feature vector, and calculate the importance of the variables. In FIG. 12, it is indicated that age is more important as a variable than gender in the estimation results by the estimation device 1. Although the components of the feature vector and the attributes of the subject, including age and gender, are used as variables in FIG. 12, the variables used to estimate TEWL may include any other variables. For example, the variables used to estimate TEWL may include moisture content of skin.

According to the estimation device 1 of the embodiment described above, a parameter related to skin function can be estimated with high accuracy. More specifically, the estimation device 1 estimates a parameter related to skin function using an estimation model constructed based on past actual measurement data in which feature vectors are associated with the parameter related to skin function. This enables the estimation device 1 to accurately estimate the parameter related to skin function using the learned estimation model. For example, the estimation device 1 can accurately estimate the parameter related to skin function using a machine learning model including a random forest model that has been learned based on the acquired past actual measurement data.

The fact that the estimation device 1 can accurately estimate the parameter related to skin function makes it possible to accurately estimate the functioning of biological tissues, including skin barrier function or the like. As a result, the estimation device 1 can be used in a wide range of fields, such as medicine and beauty, for example. For example, the estimation device 1 can contribute to diagnosing and evaluating the health of skin. The estimation device 1 can also contribute to verifying the effectiveness of skin treatment and skin care. The estimation device 1 can also contribute to predicting the onset of skin diseases.

For example, in conventional TEWL measurement, skin conductance measurement, or the like, an area of skin to be tested needs to be cleaned before measurement and the measurement needs to be performed stably in a constant temperature and humidity environment. In addition, the conventional TEWL measurement also requires the area of skin to be tested to be stationary for about 10 seconds during the measurement. As a result, the conventional technology is difficult to use in environments in which temperature and humidity cannot be controlled, or for newborns and infants whose areas of skin to be tested are difficult to hold still. Thus, the measurement device using the conventional technology was not convenient.

According to the estimation device 1 of the embodiment, a parameter related to skin function can be accurately estimated from a skin image in which unevenness of a skin surface is captured, using a method based on machine learning, so there is no need for stable measurement as in the conventional technology. In other words, a user of the estimation device 1 only needs to acquire a skin image in which unevenness of a skin surface is captured, and estimation can be performed without limiting environment or a subject. For example, the estimation device 1 can be applied to a case in which a skin image is directly acquired at a medical site, a beauty-related store, or the like, or in which a skin image of a subject in a remote area is acquired by communication. Furthermore, in some cases, it is possible to perform the estimation without washing an area of skin to be tested. As described above, the estimation device 1 improves a user's convenience in estimating a parameter related to skin function.

Since the estimation device 1 can easily present a value of a parameter related to skin function to a user, as compared to the conventional technology, the estimation device 1 can be applied to creation and use of guidelines that indicate standards, for example, what moisturizer, medication, or the like should be applied to what kind of people. In other words, unlike the conventional technology, it is possible to frequently measure a parameter related to skin function using the estimation device 1, thus facilitates the creation and use of such guidelines.

By generating a corrected image with brightness correction processing and binarization processing applied to an acquired skin image, the estimation device 1 can remove redundant information, which is not related to unevenness of a skin surface and can be noise, from the acquired skin image. This enables the estimation device 1 to estimate a parameter related to skin function more accurately.

By acquiring a series of images in step S302 of FIG. 4, the estimation device 1 can accurately separate essential information, such as topological information, from noise. For example, in the case of using only one image, it is difficult to determine which of multiple connected components and holes contained in the image are essential features and which are noise. The estimation device 1 can determine the persistence of connected components or holes in a predetermined region, for example, by acquiring a series of images by changing a threshold t in steps. Based on the persistence, the estimation device 1 can accurately separate the essential information from the noise.

The estimation device 1 extracts a feature vector based on a skin image and then estimates a parameter related to skin function using a machine learning model, as in step S202 of FIG. 3, thus reducing the number of required samples. In addition, the estimation device 1 can reduce the amount of computation. In addition, the estimation device 1 facilitates interpreting what feature of the skin image is associated with the parameter related to skin function to be estimated and the like.

The estimation device 1 estimates a parameter related to skin function based on an attribute of a subject, in addition to a feature vector, in step S203 of FIG. 3, so the estimation device 1 can estimate the parameter related to skin function more accurately according to the attribute of the subject.

It is obvious to those skilled in the art that the disclosure can be realized in predetermined forms other than the embodiment described above without departing from its spirit or its essential features. Therefore, the preceding description is exemplary and not limited to this. The scope of the disclosure is defined by the appended claims, not by the preceding description. Some changes that are within an equivalent scope, of any changes, shall be included therein.

For example, the steps in the estimation method using the above-mentioned estimation device 1 and the function and the like included in each of the steps can be rearranged so as not to logically contradict each other, and the order of the steps can be changed, some of the steps can be combined into one, or the single step can be divided.

For example, the disclosure can also be realized as a program that describes processing contents to realize each function of the above-mentioned estimation device 1 or a storage medium on which the program is recorded. It is to be understood that these are also included in the scope of the disclosure.

REFERENCE SIGNS LIST 1 estimation device
11 controller
12 communicator
13 memory
14 image acquisition unit
15 data acquisition unit
16 presentation unit
G, R2, R3, R4, R5, and R6 region
t, t1, t2, t3, t4, t5, t6, $tb_c$, $td_c$, $tb_h$, and $td_h$ threshold

The invention claimed is:

1. An estimation method for estimating a parameter related to skin function, the estimation method comprising:
an image acquisition step for acquiring a skin image in which unevenness of a skin surface is captured;
an extraction step for extracting a feature vector based on topological information on the skin image from the skin image acquired in the image acquisition step;
an estimation step for estimating the parameter related to skin function based on the feature vector extracted in the extraction step, using an estimation model constructed based on past actual measurement data in which a feature vector is associated with the parameter related to skin function; and
a presentation step for presenting the parameter related to skin function estimated in the estimation step, wherein
in the extraction step, a corrected image is generated by applying brightness correction processing and binarization processing to the acquired skin image, and
the topological information includes information regarding a zero-dimensional feature and a one-dimensional feature extracted based on the generated corrected image.

2. The estimation method according to claim 1, wherein in the estimation step, a distribution diagram illustrating persistence of each of the zero-dimensional feature and the one-dimensional feature is generated for each of the zero-dimensional feature and the one-dimensional feature, and the feature vector is extracted based on the generated distribution diagram.

3. The estimation method according to claim 1, wherein in the estimation step, the parameter related to skin function is estimated based on an attribute of a subject.

4. The estimation method according to claim 1, wherein the parameter related to skin function includes transepidermal water loss.

5. The estimation method according to claim 1, wherein the parameter related to skin function includes moisture content of skin.

6. An estimation model generation method for generating the estimation model used in the estimation method according to claim 1, the estimation model generation method comprising:
   an acquisition step for acquiring the past actual measurement data in which the feature vector is associated with the parameter related to skin function; and
   a construction step for constructing, based on the past actual measurement data acquired in the acquisition step, the estimation model to estimate the parameter related to skin function based on the feature vector.

7. The estimation model generation method according to claim 6, wherein the estimation model is a machine learning model including a random forest model learned based on the past actual measurement data acquired in the acquisition step.

8. A non-transitory computer readable medium storing a program configured to cause an information processing device to execute the estimation method according to claim 1.

9. An estimation device for estimating a parameter related to skin function, the estimation device comprising:
   an image acquisition unit configured to acquire a skin image in which unevenness of a skin surface is captured;
   a controller configured to extract a feature vector based on topological information on the skin image from the skin image acquired by the image acquisition unit, and estimate the parameter related to skin function based on the extracted feature vector using an estimation model constructed based on past actual measurement data in which a feature vector is associated with the parameter related to skin function; and
   a presentation unit configured to present the parameter related to skin function estimated by the controller, wherein
   in the extraction step, a corrected image is generated by applying brightness correction processing and binarization processing to the acquired skin image, and
   the topological information includes information regarding a zero-dimensional feature and a one-dimensional feature extracted based on the generated corrected image.

10. A non-transitory computer readable medium storing a program configured to cause an information processing device to execute the estimation model generation method according to claim 8.

* * * * *